(12) United States Patent
Callis et al.

(10) Patent No.: US 6,222,095 B1
(45) Date of Patent: Apr. 24, 2001

(54) SEQUENCES FROM AUXIN-INDUCED GENE PRODUCTS TARGETING FUSION PROTEINS FOR DEGRADATION

(75) Inventors: Judy Callis, Davis, CA (US); Cathy K. Worley, Tucson, AZ (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/064,922

(22) Filed: Apr. 22, 1998

(51) Int. Cl.[7] .......................... C12N 15/82; C12N 15/29; C12N 5/04; C12N 15/62; A01H 5/00

(52) U.S. Cl. ..................... 800/278; 536/24.1; 536/23.6; 536/23.72; 536/23.4; 800/290; 800/295; 800/298; 800/288; 435/69.1; 435/468; 435/410; 435/419; 435/69.7; 435/69.8

(58) Field of Search ................................ 536/24.1, 23.6, 536/23.1, 23.4, 23.72; 800/278, 290, 295, 288, 298; 435/69.1, 468, 410, 419, 69.7, 69.8

(56) References Cited

PUBLICATIONS

Nocker et al. J. Biological Chemistry. 1996. vol. 271: 12150–12158.*
Napoli et al. The Plant CEll. 1989. vol. 2: 278–289.*
Oeller et al. Proc. Natl. Acad. Sci. 1994, vol. 91: 326–330.*
Grant et al. Plant Cell Reports. 1995. vol. 15: 254–258.*
Glotzer, Michael et al., *Nature* 349:132–138 (1991).
Abel, S. et al. "Early auxin–induced genes encode short–lived nuclear proteins." *Proc. Natl. Acad. Sci. USA*, 91:326–330 (1994).
Abel, S. et al. "DNA elements responsive to auxin." *BioEssays*, 18.647–654 (1996).
Abel, S. and Theologis, A. "Early genes and auxin action." *Plant Physiol*. 111:9–17 (1996).
Brown, K. et al. "The signal response of IκBα is regulated by transferabel N– and C–terminal domains." *Molecular and Cellular Biology*, 17:3021–3027 (1997).
Chen, P. et al. "Multiple ubiquitin–conjugating enzymes participate in the in vivo degradation of the yeast MAT α2 repressor." *Cell*, 74:357–369 (1993).
Chen, Z. et al. "Signal–induced site–specific phosphorylation targets IκBα to the ubiquitin–proteasome pathway." *Genes and Development*, 9:1586–1597 (1995).
Clurman, B. et al. "Turnover of cyclin E by the ubiquitin–proteasome pathway is regulated by cdk2 binding and cyclin phosphorylation." *Genes and Development*, 10:1079–1990 (1996).
Cohen–Fix, O. et al. "Anaphase initiation in *Saccharomyces cerevisiae* is controlled by the APC–dependent degradation of the anaphase inhibitor Pds1p." *Genes and Development*, 10:3081–3093 (1996).

Deshaies, R.J. et al. "Ubiquitination of the $G_1$ cyclin Cln2p by a Cdc34p–dependent pathway." *EMBO J.*, 14:303–312 (1995).
Dice, J.F. "Peptide sequences that target cytosolic proteins for lysosomal proteolysis." *TIBS* 15:305–309 (1990).
DiDonato, J. et al., "Mapping of the inducible IκB phosphorylation sites that signal its ubiquitination and degradation." *Molecular and Cellular Biology*, 16:1295–1304 (1996).
Drury, L.S. et al. "The Cdc4/34/53 pathway targets Cdc6p for proteoloysis in budding yeast." *EMBO J.*, 16:5966–5976 (1997).
Ghoda, L. et al. "Prevention of rapid intracellular degradation of ODC by a carboxyl–terminal truncation." *Science*, 243:1493–1495 (1989).
Ghoda, L. et al. "Trypanosome ornithine decarboxylase is stable because it lacks sequences found in the carboxyl terminus of the mouse enzyme which target the latter for intracellular degradation." *Journal of Biological Chemistry*, 265:11823–11826 (1990).
Gil, G. et al. "Membrane–bound domain of HMG CoA reductase is required for sterol–enhanced degradation of the enzyme." *Cell*, 41:249–258 (1985).
Henchoz, S. et al. "Phosphorylation– and ubiquitin–dependent degradation of the cyclin dependent kinase inhibitor Far 1p in budding yeast." *Genes and Development*, 11:3046–3060 (1997).
Hochstrasser, M. and Varshavsky, A. "In vivo degradation of a transcriptional regulator: The yeast α2 repressor." *Cell*, 61:697–708 (1990).
Jefferson, R.A. et al. "β–Glucuronidase from *Escherichia coli* as a gene–fusion marker." *Proc. Natl. Acad. Sci. USA*, 83:8447–8451 (1986).
Jefferson, R.A. et al. "GUS fusions: β–glucuronidase as a sensitive and versatile gene fusion marker in higher plants." *EMBO J.*, 6:3901–3907 (1987).
Klotzbücher, A. et al. "The'destruction box' of cyclin A allows B–type cyclins to be ubiquitinated, but not efficiently destroyed." *EMBO J.*, 15:3053–3064 (1996).
Kornitzer, D. et al. "Regulated degradation of the transcription factor Gcn4." *EMBO J.*, 13:6021–6030 (1994).

(List continued on next page.)

*Primary Examiner*—David T. Fox
*Assistant Examiner*—Ousama Zaghmout
(74) *Attorney, Agent, or Firm*—Townsend and Townsend and Crew LLP

(57) ABSTRACT

The present invention provides isolated nucleic acid molecules comprising a polynucleotide sequence encoding a primary auxin response protein degradation signal linked to a heterologous eukaryotic polynucleotide sequence encoding a target polypeptide. Also provided are transgenic plants comprising an expression cassette comprising a polynucleotides of the invention. The invention further provides methods of targeting a recombinantly expressed target polypeptide in a plant for degradation.

49 Claims, 3 Drawing Sheets

OTHER PUBLICATIONS

Krappmann, D. et al. Different mechanisms control signal-induced degradation and basal turnover of the NF-κB inhibitor in IκBα in vivo. *EMBO J.*, 15:6716–6726 (1996).

Loetscher, P. et al. "The C terminus of mouse ornithine decarboxylase confers rapid degradation on dihydrofolate reductase." *Journal of Biological Chemistry*, 266:11213–11220 (1991).

Lu, L. et al. "Indentification of residues in ornithine decarboxylase essential for enzymic activity and for rapid protein turnover." *Biochem. J.*, 277:671–675 (1991).

Nishizawa, M. et al. "Degradation of Mos by the N-terminal proline ($Pro^2$)-dependent ubiquitin pathway on fertilization of Xenopus eggs: Possible significance of natural selection for $Pro^2$ in Mos." *EMBO J.*, 12:4021–4027 (1993).

Nishizawa, M. et al. "The 'second-codon rule' and autophosphorylation govern the stability and activity of Mos during the meiotic cell in Xenopus oocytes." *EMBO J.*, 11:2433–2446 (1992).

Orford, K. et al. "Serine phosphorylation-regulated ubiquitination and degradation of β-catenin." *Journal of Biological Chemistry*, 272:24735–24738 (1997).

Rosenberg-Hasson, Y. et al. "Characterization of sequences involved in mediating degradation of ornithine decarboxylase in cells and in reticulocyte lysate." *Biochem.*, 196:647–651 (1991).

Sadis, S. et al. "Synthetic signals for ubiquitin-dependent proteolysis." *Molecular and Cellular Biology*, 15:4086–4094 (1995).

Scheffner, M. et al. "The E6 oncoprotein encoded by human papillomavirus types 16 and 18 promotes the degradation of p53." *Cell*, 63:1129–1136 (1990).

Shanklin, J. et al. "Partial purification and peptide mapping of ubiquitin-phytochrome conjugates form oat." *Biochemistry*, 28:6028–6034 (1989).

Sun, S.-C. et al. "Both amino- and carboxyl-terminal sequences within IκBα regulate its inducible degradation." *Molecular and Cellular Biology*, 16:1058–1065 (1996).

Tyystjärvi, T. et al. "Changes of amino acid sequences in PEST-like area and QEEET motif affect degradation rate of D1 polypeptide in photosystem II." *Plant Molecular Biology*, 25:517–526 (1994).

Ward, C. et al. "Degradation of CFTR by the ubiquitin-proteasome pathway." *Cell*, 83:121–127 (1995).

\* cited by examiner

D      AMINO ACID SEQUENCE OF NLS
SYVKTVPNRTRTYIKL

SEQUENCES FROM AUXIN-INDUCED GENE PRODUCTS TARGETING FUSION PROTEINS FOR DEGRADATION

STATEMENT OF GOVERNMENT SUPPORT

This work was supported by National Science Foundation grant 93-06759. The Government may have certain rights in the invention.

FIELD OF THE INVENTION

The present invention is directed to plant genetic engineering. In particular, it relates to new methods for targeting desired recombinantly expressed polypeptides for degradation in vivo.

BACKGROUND OF THE INVENTION

The cultivation of plants has been a major focus of human activity for millennia. The development of techniques for introducing new genes into plants has now added a new dimension to this activity. Genetic engineering permits the introduction into plants of a desirable traits, such as pest or disease resistance, improved taste, improved storage characteristics, or improved ripening characteristics. Efforts are even underway to engineer plants which can act as factories to produce bulk chemicals, human therapeutics, and other commercially valuable products.

While techniques to introduce heterologous genes into plants and to obtain their expression are well known, they do not as yet permit as much control over expression as might be desired. Typically, to ensure the introduced gene is expressed, it is put under the control of a strong promoter. This may be acceptable or even desirable if the goal is merely the accumulation of high levels of the gene product. In some cases, however, the gene product may be toxic to the plant at high levels. In other instances, it may be desirable that the gene only be expressed at certain times during the plant's development, and not linger. It would therefore be desirable to have additional ways to modulate levels of gene product expression in plants.

A number of peptide regions of some short-lived proteins of organisms other than plants have been shown to operate as transferable, dominant degradation signals. Mitotic cycling contain a conserved nine amino acid sequence called the "destruction box" which is necessary for their cell cycle specific degradation (Glazer et al., 1991). A 54 amino acid peptide from sea urchin cyclic B containing the destruction box is sufficient for targeting a reporter protein for cell cycle-specific proteolysis (Glotzer et al., 1991). Two different peptide regions which were sufficient for targeting β-galactosidase for rapid degradation were identified in the yeast transcriptional repressor, MATα2 (Hochstrasser and Varshavsky, 1990). One consists of the N-terminal 67 amino acid residues and targets proteins containing it for degradation via the ubiquitin pathway (Chen et al., 1993). The N-terminal transmembrane domain of mammalian 3-hydroxy-3-methylglutaryl coenzyme A reductase (HMG-R) and of one of the yeast homologs (HMG-R-2) is necessary for its feedback regulated degradation and sufficient for targeting a reporter protein for feedback regulated degradation (Chun et al., 1990; Hampton and Rine, 1994). In response to serum deprivation, the motif KFERQ (SEQ ID NO:6) and similar peptides operate as degradation signals by targeting proteins for import into mammalian lysosomes (Dice, 1990). However, in the case of the yeast transcription factor GCN4, no small region was found to be sufficient for targeting a fusion protein for degradation suggesting that there may be a tertiary structural component to the degradation signal(s) contained within GCN4 (Kornitzer et al., 1994).

In plants a number of gene families referred here to as primary auxin response genes are known to be expressed early in plant tissues in response to the plant hormone auxin. The primary response genes are activated without a requirement for de novo protein synthesis and can be divided into 5 families based on amino acid identity and auxin induction kinetics: Aux/IAA, SAR—small auxin-unregulated, GH3-like, amino cyclopropane-1-carboxylic acid synthase (ACS), and glutathione-S-transferase (GH2/4-like) (see, Abel et al., Bases 18:647–654 (1996) and Abel et al. Plant Physiol. 111:9–17 (1996) for reviews of these plant gene families).

None of these protein sequences is known to work with respect to sequences expressed in plants. Thus, the identification of transferable peptide signals that specifically target proteins in plant cells for degradation would be desirable. The present invention provides these and other advantages.

SUMMARY OF THE INVENTION

The present invention provides isolated nucleic acid molecules comprising a polynucleotide sequence encoding a primary auxin response protein degradation signal linked to a heterologous eukaryotic polynucleotide sequence encoding a target polypeptide. Typically, the primary auxin response protein is an Aux/IAA protein, for example from Pisum sativum. A preferred Aux/IAA protein degradation signal is from PSIAA6 (SEQ ID NO:5) or PSIAA4. Fragments of the full length polypeptides can also be used.

In some embodiments, the Aux/IAA protein degradation signal includes a heterologous nuclear localization signal, for example from squash leaf curl virus BR1 protein. The polynucleotide encoding the Aux/IAA protein degradation signal can be positioned either 3' or 5' to the polynucleotide encoding the target polypeptide. In many embodiments, it is positioned 5'.

The invention also provides transgenic plants comprising an expression cassette comprising a polynucleotides of the invention. The particular plant used is not critical to the invention.

The invention further provides methods of targeting a recombinantly expressed target polypeptide in a plant for degradation. The method involve introducing into the plant a heterologous expression cassette comprising a polynucleotide sequence encoding an IAA protein degradation signal linked to a heterologous polynucleotide sequence encoding the target polypeptide, whereby a fusion protein comprising the IAA protein degradation signal linked to the target polypeptide is expressed in the plant. The recombinant expression cassette can be introduced into the plant using genetic engineering techniques or by traditional breeding methods.

DETAILED DESCRIPTION OF THE INVENTION

I. Introduction

Figure 1:
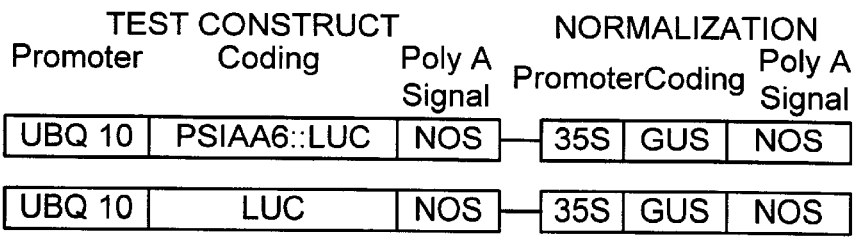
FIGS. 1A–1D are a graphical depiction of the expression cassettes used in studies documenting the invention. Panel A: L.C. Fusions. The 5' untranslated region from A. thaliana UBQ10 gene serves as the promoter with the coding sequences for PSIAA6::L.C. in-frame fusion or a cytosolicly localized LUC alone followed by the 3' untranslated region of the A. tumefaciens nopaline synthase gene (Bevan et al., 1983). Both contained a GUS expression cassette for normalization (Norris et al., 1993). Panel B: Deletion series of PSIAA6 in-frame with LUC. The PSIAA6::LUC expression cassette was altered to contain deletions of the PSIAA6 coding region. The last three clones shown included the nuclear localization signal from the squash leaf curl virus BR1 movement protein (Sanderfoot et al., 1996) at the C-termini. Both PSIAA6(18-73)::LUC clones had a methionine codon at the 5' end of the coding region to serve as a translational start site followed immediately by PSIAA6 codons 18–73. Panel C: GUS Fusions. The GUS expression cassettes were as described (Carrington et al., 1991; Abel et al., 1994; Abel and Theologis, 1995). For normalization, a second plasmid encoding peroxisomally targeted LUC was included. Panel D: Amino acid sequence of the nuclear localization signal added to the C-terminus of LUC (SEQ ID NO:7).
Figure 1:
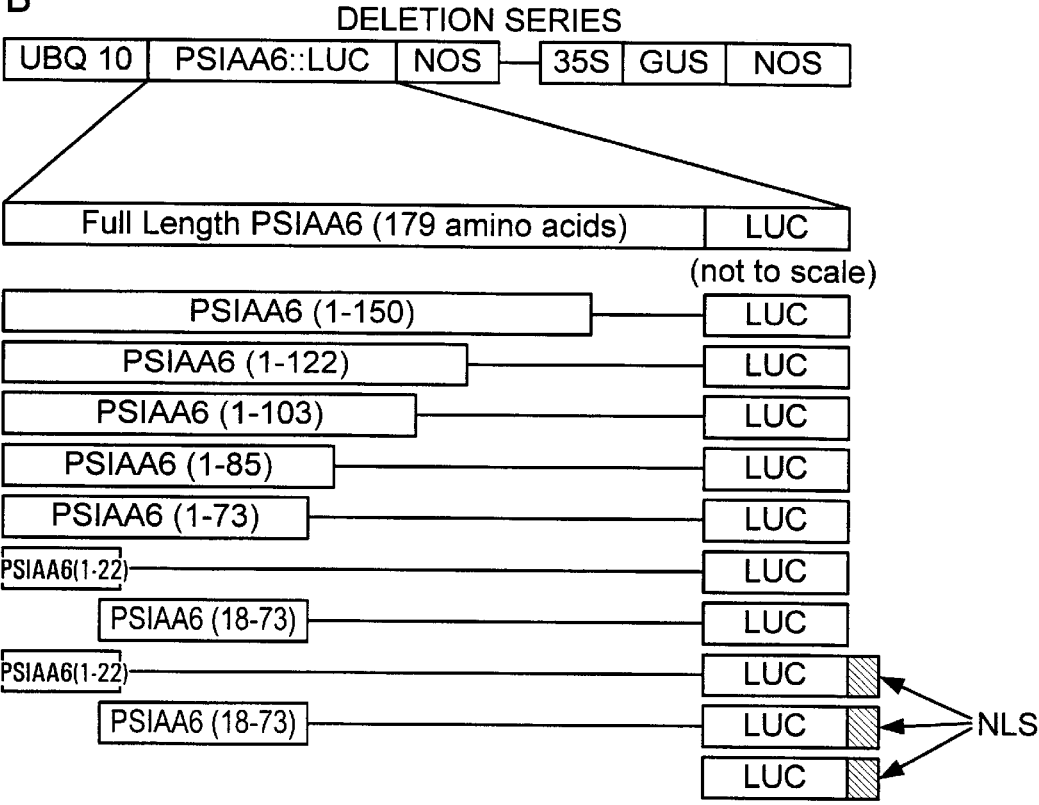
Figure 1:
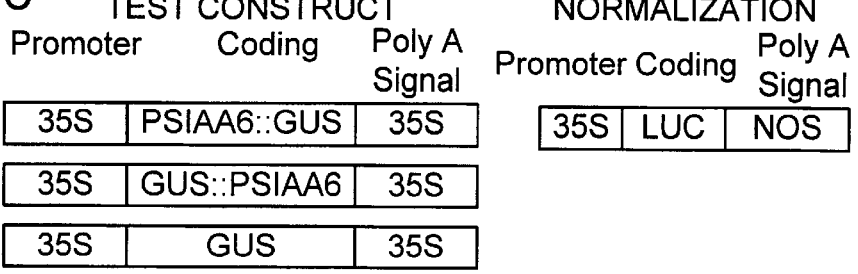

This invention provides a means of modulating expression of heterologous genes in transgenic plants, including transgenic plant cells in culture, by marking proteins expressed by those genes with a peptide signal. In particular, the invention provides polypeptide sequences which, when expressed as part of a fusion protein, mark the fusion protein for more or less rapid degradation. This permits the modulation of the half life of fusion proteins in plant cells. Thus, the extent to which they accumulate in the cell can be controlled.

Nucleotide sequences useful in the methods of the invention typically include members of the Aux/IAA family of genes, which are primary auxin response genes in plants. The plant hormone auxin is involved in a number of processes in higher plants such as, tropic responses, apical dominance, cambial cell divisions, and differentiation of vascular tissues (Went and Thimann, 1937; Goodwin, 1978; Guilfoyle, 1986; Theologis, 1986; Estelle, 1992). One of the early responses to auxin is the transcriptional activation of multiple genes. The primary response genes are activated without a requirement for de novo protein synthesis and can be divided into 5 families based on amino acid identity and auxin induction kinetics: Aux/IAA, SAR-small auxin-unregulated, GH3-like, amino cyclopropane-1-carboxylic acid synthase (ACS), and glutathione-S-transferase (GH2/4-like) (Abel et al., 1996).

The Aux/IAA family is present in diverse dicot species, and members are present in multiple organs, indicating broad expression in cells known to be affected by auxin (Abel and Theologis, 1996). The proteins encoded by two members of the Aux/IAA family, PSIAA6 and PSIAA4, have short half-lives in vivo, $t_{1/2}$ of 6 to 8 minutes, respectively (Abel et al., 1994). These degradation rates are the same independent of exogenous auxin application, indicating that the degradation machinery might be constitutively active This invention is directed to the use of polypeptides encoded by primary auxin response genes, such as members of the Aux/IAA family to modulate the half life of fusion proteins incorporating that region. As reported below, this result is demonstrated with the full length PSIAA6 gene and a number of fragments thereof.

II. Definitions

As used herein, the following terms have the meanings ascribed to them unless specified otherwise.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "primary auxin response polypeptide" and "Aux/IAA polypeptide" refer to the respective proteins encoded by genes of these families, and to fragments of those proteins.

A "polynucleotide sequence encoding a primary auxin response protein degradation signal" is a nucleic acid sequence encoding a polypeptide sequence derived from a primary auxin response gene that can mark a larger polypeptide sequence comprising the signal for more rapid degradation. Such signals may be derived from the Aux/IAA family of proteins, such as, for example, the PSIAA6 and PSIAA4 genes of pea plants. The polynucleotides of the invention can be identified as being substantially identical to the exemplified sequences described below. The sequences can also be identified by their ability to hybridize selectively to the exemplified sequences. The means for determining percent sequence identity and hybridization conditions required for these determinations are described in detail elsewhere herein. The polypeptides of the invention can also be identified by their ability to bind antibodies raised against the exemplified polypeptides.

The degradation signals of the invention can include the entire primary auxin response polypeptide sequence or a fragment thereof. Typically, the degradation signals of the invention will consist of at least about 10 amino acids, at least about 20 amino acids, at least about 30 amino acids, at least about 40 amino acids, at least about 50 amino acids and more usually at least about 60 amino acids. The signals may be the full length protein, a fragment of less than about 150 amino acids in length and more usually less than about 100 amino acids. Exemplary fragments include the first 73 amino acids of the PSIAA6 polypeptide described below. One of skill will recognize that polypeptide fragments useful in the present invention can be easily identified using the assays described in detail below.

The degradation signals of the invention desirably include a "nuclear localization signal" which may be from the same protein or may be heterologous to it. As used herein a "nuclear localization signal" is a polypeptide sequence which results in polypeptides containing the signal accumulating preferentially in the nucleus of the cell in which the polypeptide is expressed. As explained below, a common motif of nuclear localization signals is the dipeptide KR.

The term "target polypeptide" means a heterologous peptide of interest. The particular target polypeptide employed is not a part of this invention. The target polypeptide will typically confer some useful property, such as antibiotic resistance, pest or disease resistance, better taste, storage, or ripening characteristics, upon a plant or plant cell expressing the protein. As used herein, "target polypeptide" does not refer to commonly used reporter genes products such as firefly luciferase or β-glucoronidase.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants. The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated primary auxin response nucleic acid is separated from open reading frames that flank the gene and encode proteins other than a primary auxin response protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. Unless specifically limited, the term encompasses nucleic acids containing known analogues (synthetic and naturally occurring) of nucleotides, which have similar binding properties as the reference nucleic acid and are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

"Amplification" primers are oligonucleotides comprising either naturally occurring or synthetic nucleotides that can serve as the basis for the amplification of a select nucleic acid sequence. They include, e.g., polymerase chain reaction primers and ligase chain reaction oligonucleotides.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

In the case where a polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence encoding a primary auxin response gene protein degradation signal". In addition, the term specifically includes those full length sequences substantially identical (determined as described below) to an IAA polynucleotide sequence and that encode proteins that retain the short half life of the IAA polypeptide (e.g., resulting from conservative substitutions of amino acids in the promoter region of the IAA polypeptide).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95 % nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1X SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

"Antibody" refers to a polypeptide substantially encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$—$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see Paul, ed., *Fundamental Immunology* (3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

III. Description of Sequences and Proteins of the Invention

As explained above, a number of primary auxin response genes can be used in the present invention. One especially useful gene family is the Aux/IAA gene family. In a preferred embodiment of the invention, the primary auxin response gene used is the PSIAA6 gene from *Pisum sativum* (SEQ ID NO:4, GenBank Accession No. X68218).

Aux/IAA proteins contain predicted secondary structures, a ribbon-helix-helix motif, similar to that found in a class of bacterial transcriptional regulators, suggesting that Aux/IAA proteins function in the transcriptional regulation of downstream genes (Abel et al., 1996). The conserved domains found in Aux/IAA family members (Abel et al., 1994) provide a framework for deciding where to truncate the PSIAA6 protein to identify which peptide regions are useful for targeting a protein for rapid degradation. In a transient assay system, the firefly luciferase (L.C.) can be used to identify useful fragments of the invention.

As shown in the results below, both full length polypeptides and fragments encoded by members of the Aux/IAA family, such as PSIAA6, can be used to target fusion proteins for degradation. The results shown in Table 1 and FIG. 4 demonstrate that five separate, successively smaller fragments of the protein, down to the first 73 amino acid residues, worked to mark for degradation target polypeptides in fusion protein constructs with approximately the same efficiency as the full length PSIAA6 protein.

The smallest peptide region of PSIAA6 tested which was sufficient to result in decreased levels equivalent to the full length protein contained amino acids 1–73. Within this region are two domains conserved among Aux/IAA family members, as well as a basic region containing a conserved KR dipeptide which is thought to serve as part of a nuclear localization signal. A BLAST search (Altschul et al., 1990) using amino acids 1–73 to query a non-redundant data base identified many other members of this family of auxin-induced proteins from pea, Arabidopsis, mung bean, soybean, and tomato.

Persons of skill in the art will appreciate that fragments of primary auxin response gene products are likely to function as a protein degradation signal with all or most of the effect of the full length protein. Shorter polypeptides can easily be created by protein synthesis or by creating expression cassettes encoding desired amino acid residues. These shorter sequences can easily be tested by the assays taught below to determine which sequences retain function as a protein degradation signal.

Further, shorter polypeptides can also be created by deleting amino acid residues at either end of the gene product. These sequences can likewise be tested by the same assays to determine amino acid sequences shorter than amino acids 1–73 which still retain function as a protein degradation signal. Finally, having determined the effects of deletions on either end of the polypeptide, the practitioner can create and test shorter sequences by creating a polypeptide with deletions on each end of the polypeptide to determine the largest deletions which can be made which still result in a polypeptide which functions as a protein degradation signal. This series of steps will result in determining the shortest possible sequence of these polypeptides capable of acting as a protein degradation signal.

Residues 1–22 of the protein encoded by the PSIAA6 gene act as a nuclear localization signal when part of the 1–73 construct. The nuclear localization signal conferred a shorter half life on fusion proteins than was conferred upon fusion peptides lacking that section. Addition of a separate nuclear localization signal removed most of the difference in degradation speed noted between fusion proteins bearing amino acids 1–73 and those bearing 18–73. Accordingly, one means for creating fusion proteins which will degrade rapidly is to use amino acids 1–73 of the PSIAA6 gene product. In addition, as demonstrated below, nuclear localization signals from heterologous proteins can be used. Identification of suitable sequences useful for this purpose is well within the skill in the art. As explained above, nuclear localization signals often comprise the dipeptide KR. Alternatively, one can create a fusion protein with a half life somewhat shorter than normal but significantly longer than that of a fusion protein bearing the full length PSIAA6 sequence or amino acids 1–73 by placing amino acids 1–22 5' of the heterologous protein.

If a half life somewhat longer than that of the native heterologous protein is desired, one can create a fusion protein by linking amino acids 1–22 5' to the heterologous protein, and linking a nuclear localization signal 3' of the protein. Alternatively, one can accomplish the same result by linking amino acids 18–73 5' of the heterologous protein, without also linking a nuclear localization signal. See FIG. 2.

Positioning of the polypeptide within a fusion peptide can effect its activity as a protein degradation signal. As set forth in FIG. 3, a fusion of the PSIAA6 gene product with a reporter gene in the PSIAA6: :reporter gene configuration resulted in ten times lower accumulations of protein (indicating much faster degradation) than did the same fusion with the elements placed in the reporter gene::PSIAA6 configuration. Where the shortest half life is desired, it is therefore advantageous to construct the fusion proteins with the PSIAA gene or portion thereof oriented 5' to its fusion partner.

IV. Isolation of Primary Auxin Response Nucleic Acids

Generally, the nomenclature and the laboratory procedures in recombinant DNA technology described below are those well known and commonly employed in the art. Standard techniques are used for cloning, DNA and RNA isolation, amplification and purification. Generally, enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

The sequence of a number of members of the primary auxin-responsive genes are known (see, for instance, Abel and Theologis *Plant Physiol.* 111:9–17 (1996). A sequence alignment and comparison of domain structure of comparison of Aux/IAA genes can be found in Abel et al., *Proc. Natl. Acad. Soc. USA* 91:326–330 (1994). Aux/IAA gene sequences from pea are found at Genbank Accession Nos. X68217 (PSIAA6 partial cDNA sequence (SEQ ID NO:1) and encoded amino acids (SEQ ID NO:2)), X68218 (PSIAA6 genomic sequence(SEQ ID NO:3) and encoded PSIAA6 protein (SEQ ID NO:5)) and X68215 (PSIAA4). Additional sequence information for members of the family can be found as follows: for *Arabidopsis thaliana:* Genbank Accession Nos. L15448, L15449, U18406, L15450, U18407, U18408, U18409, U18410, U18411, U18412, U18413, U18414, U18415, U18416, U18417, U49072, U49073, U49074, U49075, and Conner et al., *Plant Mol. Biol.,* 15:623–632 (1990), for pea: Oeller et al., *J. Mol. Biol.,* 233:789–798 (1990), for mung bean: Genbank Accession Nos. D14412, D14413 and Yamamoto et al., *Plant Cell Physiol.,* 33:93–97 (1992), and for soybean, Ainley et al., *J. Biol. Chem.,* 263:10658–10666 (1988).

Isolation of the genes of the various primary auxin response families can be performed by a number of standard techniques. As an example, to isolate Aux/IAA nucleic acids, oligonucleotide probes based on the sequences disclosed here or in the references cited above can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from seedlings or from desired organs, such as flowers, stems, roots or hypocotyl, and a cDNA library which contains the Aux/IAA gene transcript is prepared from the mRNA. Alternatively, cDNA may be prepared from mRNA extracted from other tissues in which Aux/IAA genes or homologs are expressed.

The cDNA or genomic library can then be screened using a probe based upon the sequence of a cloned Aux/IAA gene as set forth in the references set forth above. Probes may be used to hybridize with genomic DNA or cDNA sequences to isolate homologous genes in the same or different plant species. Alternatively, antibodies raised against an Aux/IAA polypeptide can be used to screen an mRNA expression library.

Alternatively, the nucleic acids of interest can be amplified from nucleic acid samples from widely divergent plant species. For instance, polymerase chain reaction (PCR) technology can be used to amplify the sequences of the Aux/IAA genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying Aux/IAA sequences from plant tissues are generated from comparisons of the sequences provided herein. For a general overview of PCR see *PCR Protocols: A Guide to Methods and Applications.* (Innis, M, Gelfand, D., Sninsky, J. and White, T., eds.), *Academic Press,* San Diego (1990).

As noted above, the nucleic acids of the invention are characterized by the presence of sequence encoding a degradation signal. Thus, these nucleic acids can be identified by their ability to specifically hybridize to sequences encoding the signals disclosed here. Primers which specifically amplify these signals are particularly useful for identification of particular Aux/IAA polynucleotides. Primers suitable for this purpose based on the sequence of the PSIAA6 gene or other Aux/IAA genes can be designed using degenerate primers for the conserved domains shown in Abel et al., *Proc. Natl. Acad. Sci. USA* 91:326–330 (1994). Methods for designing degenerate primers are taught in *PCR Protocols,* Innis et al., supra. The conserved domains identified by these primers can then be used as probes to obtain the whole coding region.

V. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al.,*Ann. Rev. Genet.* 22:421–477 (1988). A DNA sequence coding for a fusion polypeptide comprising the Aux/IAA degradation signal linked to a desired target polypeptide will preferably be combined with transcriptional and translational initiation regulatory sequences which will direct the transcription of the sequence from the DNA in the intended tissues of the transformed plant.

As explained above the expression cassettes of the invention will include a polynucleotide encoding a desired target polypeptide. The particular target polypeptide used is not critical to the invention. The constructs of the invention can be used to modulate the half life of the target polypeptides for a number of purposes. For instance, the targeted polypeptide can be targeted for expression during a particular developmental stage of the plant, and subsequent complete degradation. Alternatively, the degradation signal of the invention may be used to control the accumulation of the fusion polypeptide such that its concentration is kept below a certain level. Exemplary target proteins include antibiotic resistance genes, such as the kanamycin resistance gene, which are introduced into transgenic plants to permit the selection of plants which have been successfully transfected. The products of these genes are needed only during the selection process and are thereafter unnecessary. Indeed, there is some concern that consumption of antibiotics in transgenic plants by animals or humans may promote the development of pathogens resistant to these antibiotics. Accordingly, controlling the levels of these gene products in transgenic plants would be desirable.

Typically, a plant promoter fragment may be employed which will direct continuous expression of the gene in tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill.

Alternatively, the plant promoter may direct expression of the fusion polypeptide in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily) in certain tissues, such as fruit, seeds, or flowers. For example, the RUBISCO small subunit promoter is under regulation by light and is expressed only in cells conducting photosynthesis. A second example, the isocitrate lyase promoter, is a strong promoter active only in seedlings.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters and coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

VI. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*—mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture,* pp. 124–176, MacMillilan Publishing Company, N.Y., 1983; and Binding, *Regeneration of Plants, Plant Protoplasts,* pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants which are responsive to auxin, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

Expressing useful genes is particularly desirable in crop plants in which seed are used directly for animal or human consumption or for industrial purposes. Examples include soybean, canola, and grains such as rice, wheat, corn, rye, and the like. It is also particularly important in plants grown for their fruit. Examples include cucumbers, tomatoes, melons, and cherries. Plants that have commercially valuable flowers, such as roses, may also benefit from use of the invention.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

If transgenic expression of the nucleic acids of the invention leads to phenotypic changes in the plants'seeds and fruit, plants comprising the expression cassettes discussed above must be sexually crossed with a second plant to obtain the final product. The seed of the invention can be derived from a cross between two transgenic plants of the invention, or a cross between a plant of the invention and another plant. The desired effects are generally enhanced when both parental plants contain expression cassettes of the invention.

EXAMPLES

The following Examples are offered by way of illustration, not limitation.

Example 1

This example shows that PSIAA6 encodes a polypeptide which targets heterologous proteins for rapid degradation.

To determine if an amino acid sequence is not only necessary for rapid proteolysis, but also sufficient for targeting a heterologous protein for degradation, it must be present in-frame with a more stable protein and shown to decrease the half-life of the entire fusion protein. The coding region for PSIAA6 was placed in-frame upstream of the coding region for a firefly luciferase lacking the C-terminal peroxisomal targeting sequence, creating PSIAA6::LUC as diagrammatically represented in FIG. 1A. This coding region is downstream of the 5' flanking region of the Arabidopsis UBQ10 polyubiquitin gene, previously shown to direct constitutive levels of marker enzyme expression in transgenic Arabidopsis (Sun and Callis, 1997). Multiple transgenic Arabidopsis plants expressing PSIAA6::LUC and unfused LUC were generated.

Pulse-chase experiments were performed on seedlings from two independent lines for both PSIAA6::LUC and LUC to determine their in vivo half-lives. In transgenic LUC expressing seedlings, the amount of labeled LUC protein after 30 minutes of chase was not reproducibly different from that at $T_0$, indicating no significant loss of protein during this time period. Assuming that differences greater than 25% could be measured, the half-life of unfused LUC was estimated at greater than one hour. In contrast, pulse-chase experiments with PSIAA6::LUC expressing seedlings revealed that significant loss of the PSIAA6::LUC protein had occurred by 30 minutes. Quantification of the signals indicated that an average of 21% of the protein present at $T_0$ was present at 30 minutes, corresponding to a half-life of 13.5 minutes.

Example 2

This example demonstrates the deletion analysis of regions of PSIAA6.

Because PSIAA6 operated as a degradation signal, enhancing the rate of LUC degradation when fused to the LUC N-terminus, the use of a transient assay system was desired to rapidly assess the in vivo effects of deletions of PSIAA6 on fusion protein stability. Cultured tobacco NT1 cells require exogenous auxin for growth, indicating that an auxin signal transduction pathway is important in these cells. In transient assays, protein levels at steady-state are proportional to half-life if synthetic rates are identical (Berlin and Schimke, 1965). Previous work from our lab using protoplasts isolated from cultured NT1 cells in transient assays established that LUC accumulation reached steady-state by 24 hrs post-transfection, and this level of activity was maintained for at least another 24 hrs. In these and previous studies, a second expression cassette encoding GUS was included to serve as a control for differences between samples in transfection and lysis efficiency (FIG. 1B).

The relative normalized activity of the full-length PSIAA6::LUC fusion protein in extracts after DNA transfection and incubation of the protoplasts to achieve steady-state enzyme activity is shown in Table 1, line 1. Steady-state LUC activity for PSIAA6::LUC fusion was 56-fold lower than the activity obtained for LUC alone, suggesting a strong destabilizing effect consistent with the short half-life of PSIAA6::LUC determined in vivo. Because differences in activity could be due to misfolding or to a reduction in catalytic efficiency itself, rather than differences in protein content, Western blot analysis was attempted to measure the protein levels directly. LUC protein was not visualized from transfected protein extracts using chemiluminescent detection, demonstrating that LUC protein concentration was below the detection limit for this method.

To determine whether there were changes in LUC specific activity as a result of addition of PSIAA6 to the N-terminus that contribute to the observed differences in enzymatic activity, LUC and PSIAA6::LUC proteins were overexpressed in yeast. LUC protein levels in these cells were sufficient to allow immunological visualization. Enzymatic activity was determined in extracts, and LUC protein content was determined by western blot analysis in samples containing equal LUC activity. The relative specific activity of PSIAA6::LUC to LUC was 52%. Using this value, the PSIAA6::LUC activity measured in protoplasts translated into a 29-fold reduction in protein level relative to LUC alone (Table 1).

Figure 2:
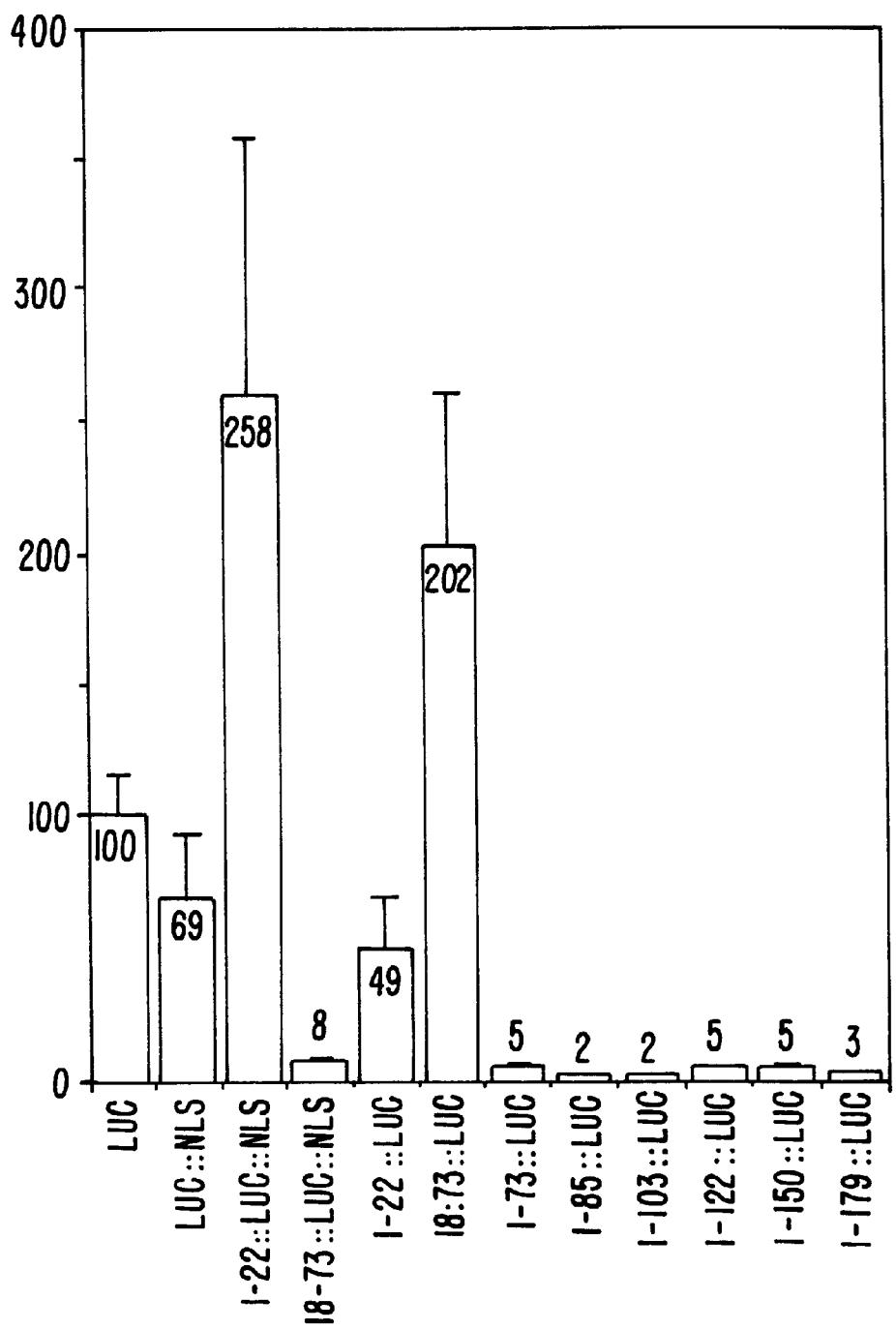
FIG. 2 is a graphical representation of the calculated relative protein concentration of the indicated fusion proteins in tobacco protoplasts. Plasmids encoding the test constructs (FIG. 1B) as well as an expression cassette for normalization were transfected into tobacco protoplasts. After transient expression, protein extracts were assayed for reporter activity. Activities for the fusion proteins were calculated as percent activity relative to the mean activity value for LUC alone. Constructs were tested in triplicate or duplicate in multiple experiments (See Table 1 for number of replicates). Relative specific activities were determined by quantitative western blot analyses, and activity levels were divided by the specific activities to yield the relative protein accumulation. The graph shows the mean value with error bars representing the standard error of the mean.

A series of C-terminal deletions of PSIAA6 were made, fused in-frame with LUC (FIG. 1), placed in the same plant expression cassette, and introduced into plant protoplasts. Protoplast extracts were analyzed for enzymatic activity as described for the full-length PSIAA6::LUC fusion (Table 1). Specific activity measurements were performed in an analogous manner (Table 1). FIG. 2 is a graphical representation of the relative protein concentration in tobacco protoplasts for the PSIAA6::LUC fusion proteins.

PSIAA6(1–150)::LUC and PSIAA6(1–122)::LUC deleted the C-terminal mono-partite NLS and both the NLS and an adjacent acidic region, respectively. Together these regions constitute domain IV which is conserved among Aux/IAA proteins (Abel et al., 1994). Both proteins were present at steady-state at 19-fold lower levels than LUC alone in the transient assay (FIG. 2). Fusion proteins PSIAA6(1–103)::LUC, PSIAA6(1–85)::LUC, PSIAA6 (1–73)::LUC represent deletions of each secondary structural element, or the entire putative baa motif, respectively. The β-sheet and N-terminal α-helix constitute Aux/IAA conserved domain III. None accumulated to levels significantly different from that of the fill length protein (Table 1 and FIG. 2).

PSIAA6(1–22)::LUC retained the conserved domain I, but deleted the bipartite NLS and the amino acids which make up the Aux/IAA conserved domain II (Abel et al., 1994). Relative concentration of this protein was comparable to LUC alone, suggesting stabilization (Table 1 and FIG. 2). Because domain I was not sufficient to operate as a degradation signal, it was deleted to determine if it was necessary for the degradation of a fusion protein. The resulting fusion protein contained amino acids 18–73 from PSLAA6 which retained the conserved residues from the bipartite NLS and domain II. PSIAA6(18–73)::LUC protein accumulated to levels which were not significantly different compared to LUC alone (Table 1 and FIG. 2). These data suggest that the smallest peptide region of PSIAA6 tested which was sufficient for targeting LUC for degradation was amino acids 1–73.

It was shown previously that amino acids 1–44 were sufficient for targeting GUS to the nucleus when fused to its N-terminus (Abel and Theologis, 1995). Therefore all proteins should be nuclear localized with the exception of PSIAA6(1–22)::LUC and PSIAA6(18–73)::LUC fusion proteins which did not retain residues proven to target a protein to the nucleus, although residues 18–73 do contain the conserved residues from one identified NLS. One possibility is that these proteins could be stabilized by virtue of their cytosolic localization. To test this hypothesis, codons for a NLS were included at the C-terminus of the PSIAA6::LUC coding region (FIG. 1). The NLS amino acid sequence was taken from the squash leaf curl virus BR1 protein, which has been proven to operate as a transferable C-terminal NLS with GUS (Sanderfoot et al., 1996). LUC with the NLS (LUC::NLS) accumulated to levels comparable to LUC alone, indicating that the NLS by itself did not affect the stability of LUC (Table 1; FIG. 2). This also demonstrated that LUC does not have a significantly different stability in the nucleus compared to the cytosol.

When an NLS was fused to the C-terminus of the PSIAA6 (18–73)::LUC, this protein was 13-fold less abundant than LUC alone and 9-fold less abundant than LUC with a C-terminal NLS alone. Amino acids 1–22 were not sufficient for targeting the fusion protein for degradation even with the NLS added. Thus, amino acids 18–73 were sufficient for targeting a nuclear LUC for degradation, and 1–73 were sufficient for targeting a LUC for degradation that does not contain an added C-terminal NLS.

ties were very low. Western blot analysis required concentrated protein samples and relatively long exposure times. For these reasons, quantitative Western blot was not possible, but clearly there was no evidence for a large accumulation of inactivated PSIAA6::GUS fusion molecules compared to GUS alone in yeast extracts with the same GUS activity. The 167-fold lower activity for the PSIAA6::GUS fusion compared to GUS alone when expressed in transfected protoplasts can not be entirely explained by a lower catalytic activity per mole of protein. These data suggest that the PSIAA6::GUS fusion protein is, indeed, accumulating to a drastically reduced level in tobacco cells compared to GUS alone.

The GUS::PSIAA6 fusion appeared to be less active—requiring more protein for equal activity in yeast extracts. Although quantitation was not possible, it is likely that most of the 3-fold reduction in activity observed was probably from enzymatic inactivation of the fusion protein. Therefore the accumulation of GUS::PSIAA6 protein in tobacco cells was likely comparable to the accumulation of GUS protein and suggested that GUS::PSIAA6 fusion protein was not degraded more rapidly than GUS in tobacco cells. Together, these data demonstrate a position effect for the degradation signal, with the PSIAA6 fusions: N-terminal fusion accu-

TABLE 1

RELATIVE SPECIFIC ACTIVITIES IN YEAST AND PROTEIN ACCUMULATION IN TOBACCO OF DIFFERENT LUC CONTAINING PROTEINS

| CONSTRUCT | % ACTIVITY | RELATIVE SPECIFIC ACTIVITY | CALCULATED RELATIVE [PROTEIN] | NUMBER OF REPEATS (N) |
|---|---|---|---|---|
| PSIAA6::LUC | 1.8 | 52 | 3.5 ± 0.73 | 11 |
| (1-150)::LUC | 3.8 | 72 | 5.3 ± 2.9 | 9 |
| (1-122)::LUC | 2.5 | 47 | 5.3 ± 1.6 | 9 |
| (1-103)::LUC | 0.57 | 24 | 2.4 ± 0.24 | 8 |
| (1-85)::LUC | 2.9 | 143 | 2.0 ± 0.58 | 8 |
| (1-73)::LUC | 4.3 | 79 | 5.4 ± 1.9 | 8 |
| (1-22)::LUC | 48 | 98 | 49 ± 20 | 8 |
| (18-73)::LUC | 52 | 26 | 200 ± 59 | 10 |
| (1-22)::LUC::NLS | 172 | 67 | 257 ± 98 | 9 |
| (18-73)::LUC::NLS | 2.2 | 28 | 7.9 ± 2.1 | 11 |
| LUC::NLS | 27 | 40 | 68 ± 25 | 8 |
| LUC | 100 | 100 | 100 ± 17 | 19 |

All values are expressed as a percentage relative to the mean value for LUC alone.

Example 3

This example demonstrates that PSIAA6 targets E. coli β-glucuronidase for rapid degradation.

Figure 3:
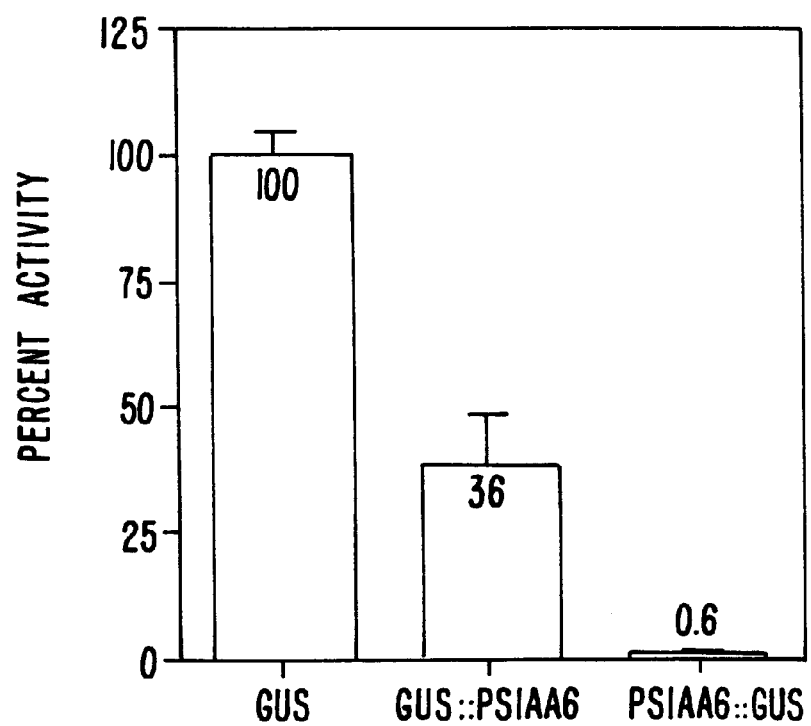
FIG. 3 is a graph of relative accumulated activity for the GUS fusions. Plasmids containing expression cassettes (FIG. 1C) were introduced into tobacco protoplasts. A plasmid containing a L.C. expression cassette was co-transfected for normalization. After transient expression, protein extracts were assayed for GUS and L.C. activity. Activities for the fusion proteins are expressed as percent activity relative to the mean activity value for GUS alone. Constructs were tested in triplicate in two separate experiments (N=6). The graph shows the mean value with error bars representing the standard error of the mean

The ability of PSIAA6 to target another commonly used plant reporter protein, GUS, for rapid proteolysis was also tested. GUS activity was measured for protein fusions that placed PSIAA6 at the N-terminus and C-terminus of GUS, named PSIAA6::GUS and GUS::PSIAA6, respectively (FIG. 1C). As shown in FIG. 3, protoplasts expressing the N-terminal fusion, PSIAA6::GUS, had a 167-fold lower GUS activity relative to protoplasts expressing GUS alone. In contrast, protoplasts expressing the C-terminal fusion, GUS::PSIAA6, showed only 3-fold lower activity compared to protoplasts expressing GUS alone (FIG. 3).

When relative specific activity determinations were attempted for the GUS fusion proteins in yeast, GUS activimulating to a much reduced level, and C-terminal fusion accumulating to a level comparable to GUS alone.

Example 4

This example provides evidence that fusion proteins bearing Aux/IAA protein degradation signals are degraded via the ubiquitin pathway.

A possible explanation for the 9-fold difference in accumulation of PSIAA6(18–73)::LUC protein and PSIAA6 (18–73)::LUC::NLS protein is that the 16 amino acids which made up the NLS could work in conjunction with amino acids 18–73 to target LUC for degradation independent of localization. If the ubiquitin pathway is responsible for the degradation of PSIAA6(18–73)::LUC::NLS, then a motif to recruit the necessary ubiquitin conjugating and/or ligating enzymes would be required as well as an accessible lysine residue for ubiquitin attachment (Chau et al., 1989). Ubiquitin attachment can be quite promiscuous with any proximal lysine serving as an attachment site (Treier et al., 1994).

The exact spatial requirements for the lysyl groups in relation to the motif which recruits a ubiquitin conjugating and/or ligating enzyme are not well-defined (Bachmair and Varshavsky, 1989) and may be different for each combination of substrate protein and ubiquitin pathway enzymes. The NLS added two lysines to the C-terminus of LUC, and the X-ray crystal structure of LUC showed that its C-terminus was proximal to its N-terminus (Conti, 1996). The addition these extra lysines could facilitate ubiquitin attachment and increase the rate of degradation of fusion proteins containing PSIAA6 or PSIAA6 derived peptides.

Ubiquitinated proteins often display a "ladder" of bands corresponding to different numbers of ubiquitin moieties attached to the substrate protein adding ~8 kDa per ubiquitin to the size of the unmodified substrate protein. Because ubiquitin moieties attach as branched chains they do not always run at perfect 8 kDa increments, and in a 12% acrylamide gel, the larger molecular weight species are not resolved well, so perfect 8 kDa increments would not be expected. The higher molecular mass bands which we detected are reasonably close to predicted sizes for PSIAA6-ubiquitin conjugates. Unresolved high molecular weight species seen were are also characteristic of polyubiquitinated substrates.

Example 5

This Example discusses the molecular techniques used in the studies resulting in the invention.

Standard molecular protocols were used for cloning (Sambrook et al., 1989). Plasmids encoding GUS [pRTL2-GUS/NIaDBam (Carrington et al., 1991), PSIAA6::GUS (Abel and Theologis, 1995), and GUS::PSIAA6 (Abel et al., 1994) were as described.

For LUC, expression cassettes containing both the coding region for the experimental LUC fusion proteins and the coding region for an unmodified GUS for normalization were cloned into a single plasmid (FIG. 1). The plant expression cassette for GUS was derived from p35SGUS (Norris et al., 1993). The promoter for the experimental LUC fusion proteins was the 5' untranslated region of the UBQ10 gene from *A. thaliana* which is constitutively expressed (Norris et al., 1993; Sun and Callis, 1997). The LUC coding region, modified with a KpnI site just upstream of the ATG, was derived from pSP-LUC+ (Promega) which encodes a luciferase enzyme with no peroxisomal targeting sequence and potential glycosylation sites mutated.

PCR of the PSIAA6 coding region of PSIAA6::GUS (Abel and Theologis, 1995) was used to amplify the desired portion of the PSIAA6 coding region, place a KpnI site at the 5' end just upstream of the start codon, and add an NcoI site at the 3' end. Plasmids for yeast expression and in planta transformation were constructed by ligating the coding region of interest into pYES2 (Invitrogen) or into pBIN19 (Clontech, Palo Alto, Calif.), respectively.

To add a nuclear localization signal to the C-terminus of LUC, PCR mutagenesis was used to amplify the LUC coding region (pSP-LUC+ template), deleting the stop codon and adding a XbaI and a PstI site to the 3' end of the PCR product. The product was ligated into bluescript KS+ (HindIII/PstI). The resulting plasmid was digested with XbaI/BamHI, and two complimentary oligos encoding the proven transferable C-terminal nuclear localization from the squash leaf curl virus movement protein BR1 (Sanderfoot et al., 1996) were ligated into the XbaI/BamHI overhangs:

oligo #1:
5' CTAGATCTTACGTTAAGACTGTTCCAAA-CAGAACTAGAACTTACAT CAAGTTCTGAG 3' (SEQ ID NO:8)

oligo #2:
5' GATCCTCAGAACTTGATGTAAGT-TCTAGTTCTGTTTGGAACAGTCTTAACGTA AGAT 3' (SEQ ID NO:9).

Loss of the PstI site verified the new clones, and they were sequenced from the 3' end through an internal AvaI site in the LUC coding region. The AvaI/BamHI fragment from this modified LUC was substituted for cLUC in the transient expression plasmid.

Example 6

This example describes the transient expression, protein extracts and enzyme activity assays used in the studies resulting in the invention.

Plasmids used for transfection into protoplasts were harvested by alkaline lysis of large scale preparations and purified by polyethylene glycol precipitation (Sambrook et al., 1989). PEG-mediated DNA transfer into protoplasts derived from NT1 tobacco cells was performed as described by Altman et al. (Altman et al., 1992). 50 mg of the plasmid encoding GUS, PSIAA6::GUS or GUS::PSIAA6 were co-transfected with 50 mg of the plasmid containing the 35S-LUC-NOS expression cassette for normalization. For the LUC fusion encoding plasmids, 100 mg of a single plasmid encoding both the experimental protein as well as a second reporter for normalization was used (FIG. 1). Protoplasts were incubated for 24–48 hours; during this time period LUC levels were at steady-state. Cells were lysed by sonication in 300 mL extraction buffer (100 mM potassium phosphate pH 7.8, 1 mM EDTA, 7 mM βME, 1 mM PMSF, and 20 mg/mL each of antipain, aprotinin, chymostatin, leupeptin, and pepstatin A), spun at 10,000 g at 4° C. for 10 minutes, and supernatants were used for assays.

Duplicate LUC activity assays were performed as described (Norris et al., 1993). Duplicate luminescent GUS activity assays were performed with the GUSLIGHT Kit (TROPIX, Bedford, Mass.) according to the manufacturer's instructions. Significant difference between samples described in the text refers to >95% probability based on the Student's t test.

Example 7

This example discussses yeast expression and Western blot analysis used in the studies reported herein.

Plasmids encoding the desired fusion proteins were transformed into *S. cerevisiae* strain WCG4a (Richter-Ruoff et al., 1994) using the lithium acetate method (Ito, 1983) with URA3 selection. After galactose induction, cells were lysed in 300 mL LUC extraction buffer (see above) by glass bead agitation. Extracts were spun at 10,000×g at 4° C. for 10 minutes, and $A_{280}$ of the supernatant was measured to determine relative total protein content (Bollage and Edelstein, 1991). Protein concentration was verified by SDS-PAGE and Coomassie blue staining. Supernatants were diluted with extraction buffer to equal $A_{280}$, and 1:10,000 dilutions were assayed for LUC activity or GUS activity. Linearity of the assay was verified with serial dilutions of the supernatant.

Yeast extracts containing equal reporter activity and equal total protein were prepared for SDS-PAGE and Western blotting (Beers et al., 1992). Equal total protein between extracts was achieved by addition of negative control yeast extract to samples with lower protein content. Anti LUC (Cortex Biochem) and anti-GUS (Dr. Tom McKnight, Texas A&M University) polyclonal antibodies were used to visualize their respective immunogens by chemiluminescence (Gallaher et al., 1994). Signal was quantitated by densitometry, and the dilution series verified linearity of the signal. Each construct was expressed in two independently transformed yeast strains for specific activity determination. Two separate blots were performed for each construct (data not shown), and their densitometry values averaged.

Example 8

This example describes in planta transformation techniques.

*A. thaliana* ecotype No-0 plants were transformed by the in planta method (Bechtold et al., 1993; Bent et al., 1994). Three homozygous transgenic lines expressing UBQ10-PSIAA6::LUC-NOS and two homozygous lines expressing UBQ10-LUC-NOS were subsequently generated.

Example 9

This example describes pulse-chase analysis.

Transgenic Arabidopsis seedlings expressing LUC and PSIAA6::LUC were used for pulse-chase experiments 5–7 days after imbibition. Seedlings were incubated with 700 mCi of $^{35}S$ labeled methionine and cysteine (NEN EASYTAG) for 2 hours, and chased with 1 mM cysteine, 1 mM methionine, and 200 mg/mL cycloheximide in $H_2O$. At each time point, seedlings were ground in ice-cold NP-40 extraction buffer: 150 mM NaCl, 1.0% Nonidet P-40, 50 mM Tris (pH 8) and 1 mM EDTA (Harlow and Lane, 1988) containing a protease inhibitor cocktail (final concentration: 1 mM phenylmethylsulfonyl fluoride (PMSF) and 20 mg/mL each of antipain, aprotinin, chymostatin, leupeptin, and pepstatin A).

LUC and PSIAA6::LUC were immunoprecipitated from aliquots of the cleared supernatants containing equal TCA precipitable counts for $T_0$ and $T_{30}$ samples using 10 mL anti-LUC antibodies (Cortex Biochem) and 50 mL PAN-SORBIN cells (Calbiochem) following standard protocols (Harlow and Lane, 1988). The precipitates were separated by SDS-PAGE in 7% polyacrylamide gels, and were exposed to phosphorimaging plates for 24 hours. Imaging plates were scanned on a Fuji-imager, and bands were quantitated using the MacBas program. Pulse-chase analysis was performed two different times with two different transgenic lines for each transgene.

Example 10

This example demonstrates the preparation of pea extracts.

Etiolated, 7 day old *Pisum sativum c.* Alaska seedlings were removed from vermiculite and immersed in a solution of 10 mM indole-3-acetic acid (IAA) in the dark. After 2 hours of incubation in IAA solution, stem segments about 1 cm long were excised from just above the root and just below the apical hook. Tissue was frozen at −80° C. for future use. Frozen tissue was ground in a chilled mortar and pestle in ice cold NP-40 buffer (see above) containing a protease inhibitor cocktail (1 mM PMSF, 5 mM NEM, and 20 mg/mL each of antipain, aprotinin, leupeptin, and pepstatin A). Extracts were cleared by centrifuging at 10,000×g at 4° C. for 10 minutes, and supernatants were used for experiments.

Example 11

This example demonstrates antibody preparation and use.

Antibodies against ubiquitin were raised in a chicken at the Berkeley Antibody Company and harvested from the egg yolks (Song et al., 1985). For affinity purification, ubiquitin was cross linked to affigel-10 (Bio-Rad), and the resulting immobilized ubiquitin was used to purify anti-ubiquitin antibodies from the IgY mixture using standard protocols (Harlow and Lane, 1988). 600 mg of pre-immune IgYs and affinity purified anti-ubiquitin IgYs were cross-linked to Affi-Gel Hz agarose beads (Bio-Rad) according to the manufacturer's instructions. 20 mL of pea extract containing 200 mg total protein was incubated with immune and pre-immune beads. Beads were rinsed with 10 mM $KPO_4$ pH 7.5 until no protein was detected by $A_{280}$. Beads were boiled in 1 mL 1% SDS in 10 mM Tris pH 8.0, and 300 mL aliquots representing equal fractions of the bound proteins were acetone precipitated and resuspended in SDS sample buffer for SDS-PAGE and western blot analysis. Rabbit Anti-sera to PSIAA6 was affinity purified using a GST-PSIAA6 fusion protein immobilized on glutathione-agarose beads and used at 1:60 dilution.

The anti-PSIAA6 blot was stripped of anti-PSIAA6 antibodies and secondary antibodies by soaking briefly in methanol, rinsing in TBS (50 mM Tris-HCl pH 7.4 and 200 mM NaCl), incubating in 5 mM $NaPO_4$ pH 7.5, 2% SDS, and 2 mM b-mercaptoethanol for 30 min. at 60° C., followed by 3 rinses in TBS. The PVDF membrane was autoclaved in semi-dry transfer buffer prior to incubation with primary antibody for the anti-ubiquitin western blots. Affinity purified rabbit anti-ubiquitin antibodies (Beers et al., 1992) were used at a 1:10,000 dilution.

REFERENCES CITED

Abel et al., *BioEssays* 18:647–654 (1996)
Abel, et al., *Proc. Natl. Acad. Sci. USA* 91:326–330 (1994).
Abel, et al., *Plant J.* 8:87–96 (1995).
Abel, et al., *Plant Physiol.* 111:9–17.
Abler, et al., *Plant Mol. Biol.* 32:63–78 (1996).
Ainley et al., *J. Biol. Chem.* 263:10650–10666 (1988).
Alhanaty, et al., *Curr. Top. in Cellular Regulation* 27:267–278 (1985).
Altman, T. et al., In Methods in Arabidopsis Research, C. Koncz, N.-H. Chua and J. Schell, ed (Singapore: World Scientific), pp. 310–330 (1992).
Altschul, et al., *J. Mol. Biol.* 215:403–410 (1990).
Bachmair, et al., *Cell* 56:1019–32 (1989).
Bechtold, et al., *C. R. Acad. Sci. Paris, Life Sciences* 316:1194–1199 (1993).
Beers, et al., *J. Biol. Chem.* 267:15432–15439 (1992).
Bent, et al., *Science* 265:1856–1860 (1994).
Berlin, et al., *Molecular Pharmacology* 1:149–156 (1965).
Bevan, M. *Nucl. Acids Res.* 11:369–385 (1983).
Bollage, et al., In Protein Methods, D. M. Bollage and S. J. Edelstein, ed (New York: Academic Press), pp. 45–69 (1991).
Carrington, et al., *Plant Cell* 3:953–962. (1991).
Chau, et al., *Science* 243:1576–1583 (1989).
Chen, et al., *Cell* 74:357–369 (1993).
Connor et al., *Plant Mol. Biol.* 15:623–632 (1990).
Conti, et al., *Structure* 4:287–298 (1996).
Dice, *TIBS* 15:305–309 (1990).
Estelle, *BioEssays* 14:439–444 (1992).
Gallaher, S. et al., In Current Protocols in Molecular Biology, F. M. Ausubel, R. Brent and R. E. Kingston, ed (New York: Greene Publishing Associates and Wiley-Interscience), pp. 10.8.1–10.8.17 (1994).
Glotzer, et al., *Nature* 349:132–138 (1991).
Goldberg, et al., *Annu. Rev. Biochem.* 45:747–803 (1976).
Guilfoyle, *CRC Crit. Rev. Plant Sci.* 4:247–276 (1986).
Harlow, E. et al., Antibodies: A Laboratory Manual. (Cold Spring Harbor: Cold Spring Harbor Laboratory), pp. 505 (1988).

Hegde, et al., *Proc. Natl. Acad. Sci. USA* 90:7436–7440 (1993).
Hochstrasser, *Annu. Rev. Genet.* 30:405–439 (1996).
Hochstrasser, et al., *Cell* 61:697–708 (1990).
Hofmann, F. *Genes and Development* 10:2949–2959 (1996).
Ito, et al., *J. of Bact.* 153:163–168 (1983).
Kim, et al., *Proc. Natl. Acad. Sci. USA* 94:11786–11791 (1997).
Kornitzer, et al., *EMBO J.* 13:6021–6030 (1994).
Koshiba, et al., *J. Mol. Biol.* 253:396–413 (1995).
Norris, et al., *Plant Mol. Biol.* 21:895–906 (1993).
Oeller et al., *J. Mol. Biol.* 233:789–798 (1993).
Richter Ruoff, et al., *FEBS Letters* 354:50–52 (1994).
Rogers, et al., *J. Biol. Chem.* 263:19850–19862 (1988).
Sambrook, J. et al., Molecular Cloning: a Laboratory Manual. (Plain View, N.Y.: Cold Spring Harbor Laboratory Press) (1989).
Sanderfoot, et al., *Plant Physiol.* 110:23–33 (1996).
Scheffner, et al., *Cell* 63:1129–1136 (1990).
Shanklin, et al., *Proc. Natl. Acad. Sci. USA* 84:359–363 (1987).
Song, et al., *J. Immunol.* 135:3354–3359 (1985).
Sun, and Callis, *The Plant Journal* 11:101–111 (1997).
Theologis, *Ann. Rev. Plant Physiol.* 37:407–438 (1986).
Thompson, et al., *Gene* 103:171–177 (1991).
Treier, et al., *Cell* 78:787–798 (1994).
Ulmasov, et al., *Science* 276:1865–1868 (1997a).
Ulmasov, et al., *The Plant Cell* 9:1963–1971 (1997b).
Went, et al., Phytohormones (New York: Macmillan) (1937).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated nucleic acid molecule comprising a polynucleotide sequence encoding a primary auxin response protein degradation signal linked to a heterologous eukaryotic polynucleotide sequence encoding a target polypeptide.

2. The nucleic acid molecule of claim 1 encoding an Aux/IAA protein degradation signal.

3. The nucleic acid molecule of claim 2, wherein the polynucleotide sequence encoding the Aux/IAA protein degradation signal is from a legume.

4. The nucleic acid molecule of claim 3, wherein the polynucleotide sequence encoding the Aux/IAA protein degradation signal is from *Pisum sativum*.

5. The nucleic acid molecule of claim 4, wherein the polynucleotide sequence encoding the Aux/IAA protein degradation signal is PSIAA6.

6. The nucleic acid molecule of claim 4, the polynucleotide sequence encoding the Aux/IAA protein degradation signal is PSIAA4.

7. The nucleic acid molecule of claim 2, wherein the polynucleotide encoding the Aux/IAA protein degradation signal is as shown in SEQ ID NO:4.

8. The nucleic acid molecule of claim 2, wherein the Aux/IAA protein degradation signal element encoded comprises residues 1–150 of SEQ ID NO:5.

9. The nucleic acid molecule of claim 2, wherein the Aux/IAA protein degradation signal element encoded comprises residues 1–122 of SEQ ID NO:5.

10. The nucleic acid molecule of claim 1, wherein the IAA protein degradation signal encoded comprises residues 1–103 of SEQ ID NO:5.

11. The nucleic acid molecule of claim 1, wherein the IAA protein degradation signal encoded comprises residues 1–85 of SEQ ID NO:5.

12. The nucleic acid molecule of claim 1, wherein the IAA protein degradation signal encoded comprises residues 1–73 of SEQ ID NO:5.

13. The nucleic acid molecule of claim 1, wherein the IAA protein degradation signal encoded comprises residues 1–50 of SEQ ID NO:5.

14. The nucleic acid molecule of claim 1, wherein the IAA protein degradation signal includes a heterologous nuclear localization signal.

15. The nucleic acid molecule of claim 14, wherein the nuclear localization signal is from a squash leaf curl virus BR1 protein.

16. The nucleic acid molecule of claim 1, wherein the polynucleotide encoding the Aux/IAA protein degradation signal is positioned 5' to the polynucleotide encoding the target polypeptide.

17. A transgenic plant comprising an expression cassette comprising a polynucleotide sequence encoding an Aux/IAA protein degradation signal linked to a heterologous polynucleotide sequence encoding a target polypeptide.

18. The transgenic plant of claim 17, which is pea.

19. The transgenic plant of claim 17, provided that the target polypeptide is not firefly luciferase or β-glucoronidase.

20. The transgenic plant of claim 17, wherein the polynucleotide sequence encoding the Aux/IAA protein degradation signal is from a legume.

21. The transgenic plant of claim 17, wherein the polynucleotide sequence encoding the Aux/IAA protein degradation signal is from *Pisum sativum*.

22. The transgenic plant of claim 17, wherein the polynucleotide sequence encoding the Aux/IAA protein degradation signal is PSIAA6.

23. The transgenic plant of claim 17, wherein the IAA protein degradation element is PSIAA4.

24. The transgenic plant of claim 17, wherein the polynucleotide encoding the IAA protein degradation signal is as shown in SEQ ID NO:4.

25. The transgenic plant of claim 17, wherein the IAA protein degradation signal element encoded comprises residues 1–150 of SEQ ID NO:5.

26. The transgenic plant of claim 17, wherein the IAA protein degradation signal element encoded comprises residues 1–122 of SEQ ID NO:5.

27. The transgenic plant of claim 17, wherein the IAA protein degradation signal encoded comprises residues 1–103 of SEQ ID NO:5.

28. The transgenic plant of claim 17, wherein the IAA protein degradation signal encoded comprises residues 1–85 of SEQ ID NO:5.

29. The transgenic plant of claim 17, wherein the IAA protein degradation signal encoded comprises residues 1–73 of SEQ ID NO:5.

30. The transgenic plant of claim 17, wherein the IAA protein degradation signal encoded comprises residues 1–50 of SEQ ID NO:5.

31. The transgenic plant of claim 17, wherein the IAA protein degradation signal includes a heterologous nuclear localization signal.

32. The transgenic plant of claim 17, wherein the nuclear localization signal is from a squash leaf curl virus BR1 protein.

33. The transgenic plant of claim 17, wherein the polynucleotide encoding the Aux/IAA protein degradation signal is positioned 5' to the polynucleotide encoding the target polypeptide.

34. A method of targeting a recombinantly expressed target polypeptide in a plant for degradation, the method comprising introducing into the plant a heterologous expression cassette comprising a polynucleotide sequence encoding an IAA protein degradation signal linked to a heterologous polynucleotide sequence encoding the target polypeptide, whereby a fusion protein comprising the IAA protein degradation signal linked to the target polypeptide is expressed in the plant.

35. The method of claim 34, provided that the target polypeptide is not firefly luciferase or β-glucoronidase.

36. The method of claim 34, wherein the polynucleotide sequence encoding the Aux/IAA protein degradation signal is from a legume.

37. The method of claim 34, wherein the polynucleotide sequence encoding the Aux/IAA protein degradation signal is from *Pisum sativum*.

38. The method of claim 34, wherein the polynucleotide sequence encoding the Aux/IAA protein degradation signal is PSIAA6.

39. The method of claim 34, wherein the IAA protein degradation element is PSIAA4.

40. The method of claim 34, wherein the polynucleotide encoding the IAA protein degradation signal is as shown in SEQ ID NO:4.

41. The method of claim 34, wherein the IAA protein degradation signal element encoded comprises residues 1–150 of SEQ ID NO:5.

42. The method of claim 34, wherein the IAA protein degradation signal element encoded comprises residues 1–122 of SEQ ID NO:5.

43. The method of claim 34, wherein the IAA protein degradation signal encoded comprises residues 1–103 of SEQ ID NO:5.

44. The method of claim 34, wherein the IAA protein degradation signal encoded comprises residues 1–85 of SEQ ID NO:5.

45. The method of claim 34, wherein the IAA protein degradation signal encoded comprises residues 1–73 of SEQ ID NO:5.

46. The method of claim 34, wherein the IAA protein degradation signal encoded comprises residues 1–50 of SEQ ID NO:5.

47. The method of claim 34, wherein the IAA protein degradation signal includes a heterologous nuclear localization signal.

48. The method of claim 47, wherein the nuclear localization signal is from a squash leaf curl virus BR1 protein.

49. The method of claim 34, wherein the polynucleotide encoding the Aux/IAA protein degradation signal is positioned 5' to the polynucleotide encoding the target polypeptide.

* * * * *

UNITED STATES PATENT AND TRADEMARK OFFICE
CERTIFICATE OF CORRECTION

PATENT NO. : 6,222,095 B1  
DATED : April 24, 2001  
INVENTOR(S) : Judy Callis et al.

Page 1 of 1

It is certified that error appears in the above-identified patent and that said Letters Patent is hereby corrected as shown below:

<u>Column 1,</u>
Beginning at line 9, delete

"This work was supported by National Science Foundation grant 93-06759. The Government may have certain rights in this invention."

and insert

-- This invention was made with Government support under Grant Nos. IBN9158453 and IBN93X06759, awarded by the National Science Foundation. The Government has certain rights in this invention. --

Signed and Sealed this

Fifth Day of March, 2002

*Attest:*

JAMES E. ROGAN
*Attesting Officer*  *Director of the United States Patent and Trademark Office*

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 702 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 2..472
       (D) OTHER INFORMATION: /product= "auxin-induced protein"
           /note= "clone pIAA6 partial cDNA for
           Pisum sativum auxin-induced protein,
           CDS <2..472"

(xi) SEQUENCE DESCRIPTION: SEQ ID NO: 1:

```
G AAG AAT GAG AAG AAG AGG ATG TTC TCG GAG ATC GAC GGT GGT GTG         46
  Lys Asn Glu Lys Lys Arg Met Phe Ser Glu Ile Asp Gly Gly Val
  1               5                  10                  15

GAA GAA AAT GGA GGC TCC GGT GAT CGG AAA AGT GTC GAT AAG AAG AAT        94
Glu Glu Asn Gly Gly Ser Gly Asp Arg Lys Ser Val Asp Lys Lys Asn
             20                  25                  30

CAA GTT GTC GGG TGG CCT CCG GTG TGC TCG TAC CGG AAG AAG AAC ATG       142
Gln Val Val Gly Trp Pro Pro Val Cys Ser Tyr Arg Lys Lys Asn Met
         35                  40                  45

AAT GAA GGT TCG AAA ATG TAT ATG AAG GTT AGC ATG GAT GGA GCT CCT       190
Asn Glu Gly Ser Lys Met Tyr Met Lys Val Ser Met Asp Gly Ala Pro
     50                  55                  60

TAC TTG CGT AAG ATT GAT CTT TGT TTG CAT AAG GGT TAC TTG GAG TTA       238
Tyr Leu Arg Lys Ile Asp Leu Cys Leu His Lys Gly Tyr Leu Glu Leu
 65                  70                  75

GCT TTG GCT TTG GAG AAG CTC TTT GAT TGT TGT GGA ATT GAA GAG GCA       286
Ala Leu Ala Leu Glu Lys Leu Phe Asp Cys Cys Gly Ile Glu Glu Ala
 80                  85                  90                  95
```

```
TTA AAG GAT GCA GAA AAT TGT GAA CAC GTT CCA ATT TAT GAG GAC AAA       334
Leu Lys Asp Ala Glu Asn Cys Glu His Val Pro Ile Tyr Glu Asp Lys
            100                 105                 110

GAT GGT GAT TGG ATG CTG GTT GGA GAT GTC CCT TGG GAG ATG TTT ATT       382
Asp Gly Asp Trp Met Leu Val Gly Asp Val Pro Trp Glu Met Phe Ile
            115                 120                 125

GAG TCA TGC AAG AGG CTG AGG ATT ATG AAG AGG TCA GAT GCA AAG GGC       430
Glu Ser Cys Lys Arg Leu Arg Ile Met Lys Arg Ser Asp Ala Lys Gly
            130                 135                 140

TTT GAT TTG CAA CCA AAA GGA TCT TTG AAG AGA TTC ATA TAGAAAGTGA        479
Phe Asp Leu Gln Pro Lys Gly Ser Leu Lys Arg Phe Ile
            145                 150                 155

AAGATATGTT AGGGTTCTAA ACAATGAAAA AGTTGTTAAT TTGGATTTTA TGTTGTTTTT     539

TAATTATATT TGAGAAGCAT TCCTTTATAC TATAGTTTGA TATGAATGAA CTAGGGTTTT     599

ATCATCATGT TTATTTTAAT GTTTATATA TCAAAGATAT ATAGGATCAA TTTTTATTAT      659

GGATTTAAAG GATATGTATT GTGAGTGTTA TTTTGAAAAA AAA                       702
```

(2) INFORMATION FOR SEQ ID NO: 2:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO: 2:

```
Lys Asn Glu Lys Lys Arg Met Phe Ser Glu Ile Asp Gly Val Glu
 1               5                  10                  15

Glu Asn Gly Gly Ser Gly Asp Arg Lys Ser Val Asp Lys Lys Asn Gln
                20                  25                  30

Val Val Gly Trp Pro Pro Val Cys Ser Tyr Arg Lys Lys Asn Met Asn
            35                  40                  45

Glu Gly Ser Lys Met Tyr Met Lys Val Ser Met Asp Gly Ala Pro Tyr
    50                  55                  60

Leu Arg Lys Ile Asp Leu Cys Leu His Lys Gly Tyr Leu Glu Leu Ala
65                  70                  75                  80

Leu Ala Leu Glu Lys Leu Phe Asp Cys Cys Gly Ile Glu Glu Ala Leu
                85                  90                  95

Lys Asp Ala Glu Asn Cys Glu His Val Pro Ile Tyr Glu Asp Lys Asp
            100                 105                 110

Gly Asp Trp Met Leu Val Gly Asp Val Pro Trp Glu Met Phe Ile Glu
            115                 120                 125

Ser Cys Lys Arg Leu Arg Ile Met Lys Arg Ser Asp Ala Lys Gly Phe
130                 135                 140

Asp Leu Gln Pro Lys Gly Ser Leu Lys Arg Phe Ile
145                 150                 155
```

(2) INFORMATION FOR SEQ ID NO: 3:

(i) SEQUENCE CHARACTERISTICS:
        (A) LENGTH: 5923 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS (B) LOCATION: join(2667..3012, 4327..4420, 4778..4877)
(D) OTHER INFORMATION: /product= "PSIAA6 auxin-induced
    protein"
    /note= "gene for PS-IAA6 (indoleacetic
    acid-inducible gene of pea
    (Pisum sativum))"

(xi) SEQUENCE DESCRIPTION: SEQ ID NO: 3:

```
TTTAGCTCAT GGCCTCTACT ATGCTTGCCC CGCCTCACTT TTTTTTGCAA GGAGAGCCTA        60
AACAAGGCGA ACATGCCTCT TTTCCACCCC TAGTTGTCAT GTTGCAACAC CTCTAGTGGA       120
GTTGTGATAT GAGTATGATT CTTTTGTTAA TTCTCTTTAA CGCGGAAGAG TCTCACATTT       180
TATTTTTGTA CAAAACTGAA TATGGTCAAC ATGAGTTCAC TTACACCATG TACTCTTAGT       240
GAGACTTGAC GTTGTTGAAT GTCATGTGAC AATTCGGGTC TTGAGGATTG GAAAGGTGGG       300
AAAGGAGGAT GGTTATGATG CAGGAATGTA TAAGATCAAT TATTATTCTT GAACAATCGG       360
TTGGGGTATT GTGATTGAAT CTTTGAGATT CTGATGAAGC AAAGGTTCTT TAGTTGGAAA       420
GGTGAGAACT AATGTTACGT TGTCTTCGAA GATCTGAATC ATTGATCTAA TGGCAAGAAA       480
TCATTATGGG GTCGAGTTGC TCTAGAACCA GCTATTTGAG GAGATAATGT GAACATGAAC       540
AACATTTAAT AAATGATTAC AGTGATCAGA ACGATTAATA TAAGCAGTTG CAGAGGTGCA       600
ACAGAGAAGA TCTATATATAT TCAATGGAAA ATTTGTTAGA ATCATAAGAT GATTGGTGCC       660
TTATTATGTA GTGGAACATA TAATGGATAA CAAGTTGAAA ATGGAGACTG TAGAAAGGCT       720
TTTGGTATGG TGGGTGTGGT CTCTACTAAT TAGAGACATG TGAGTACTTG CAAGGTTAAC       780
ACTCCAATGC TAAAGTCTAT ATTTGATAGA GGTAAAACTG ATGCAAGTAT AAGTGGGTGA       840
ATACATGGGC ATGACCCCAA GCGACACTTA TATAGGGATG ACAGTTAGAA CTGCTCCGGT       900
TGATCAAACT TTGATTGAGA AGGATTATTA GATGCATATA AATGAATTTG TTTAGAACAT       960
GAACCATGCG CTTATGCGAC ACTCCAAAAT GGAGGTCCAC CTGTACCTCA GTCCACTGAA      1020
ATGCTTTGGA TAGATTCGAT CGTTGGATTG AGCCGATCTC ATTGGACTTT GGTCAACATT      1080
ATTAGAGTTT GACCTAACTT ATCCTTACAA AACCGACTTG TAAGGTGAGA GGTGTCACTC      1140
TATATAAACT CTTTTAAAAC TCTATGTTTA ACCAATGTGG AACTTGAGAT CTTTCTAATA      1200
CATCCCTCAT GCTTAACTTT TTTTTTGAGC TTGGTGCGTG AATTTTAAAT GGTGGGTGAT      1260
CTATGGTTTG ATCGATAGGC TTGATACTAT ATTAAAGTTT GACCTAACTC ATCCTTAAAA      1320
AATTGACTTG TAAGGTAAGA AGTGGCATCC TATATAAACT TTTTTTAAAC TCTATATCTA      1380
ATCAGTGTGA GACTTGAGAT ATTCTCCATA AATACAATAT AACATTAAAA AAGAAAGACG      1440
AGTCCTTAAT TTATTATTTG ATTATGATCG GATTAGCAAG TTTATTTTCT CAAATAATTA      1500
AAATTTTAGA TGCTCTTAGT ATCGTAGAAA AAATCAAGAT CAAGAATTGG CCGTGAATCT      1560
TTAGTAGGTG TAAGAATCAT TTTGCTTAAT TTACTATCAT GCTATGTCAA CCATCTAGAT      1620
TGTTTACATA AGGGCAACCC TCCACTTTAT CTTTGTTATA CCCTTATACC AATTCTCCTT      1680
TACCGGTTGT ATTATTATAA TATTTCTTAA TTTATTTGAT TCAAGTGAAG GAGATTCTAT      1740
TGTAGGATCT TCTATGGTGT TGCTAGCATT AAGTGGTAGT TGTGTGATTT ATGACATAGG      1800
AGAGGATACG CGTTTGATAA GTCTCAATGT GTTTCCTGGT CCTAAGGATT GTCTAGTTTG      1860
ACTGAATTGC TTTGATGTGA TCATTCACAG CTCACACAAG GAATTTCCTT TAGGTCCTAC      1920
CTACTTAATT GTTCATTTCA TTTCAGTTCC TTGCAGCAGC ATCAACATCA TATGCATGTC      1980
CAATATCTAT GTTATATGGA TATGTCACAT CCTTTGTGGC ATGGCATACT GCCATTAATT      2040
GATCATAATC GTGTAATTAC CATAGTATGA CATAGCATTT TAATTTTTTA ATTTTATATA      2100
```

```
TATATATATA TATATATTTA TATAATATTT TCTGTAAATT TTAATAAAAT ATTAAATTTA        2160

TTATTCAATT ATTTTAAGTT TATATTTTTA TGAAAAATGA TAAAAGTCCA TTTTTAGATT        2220

TTTTATATTT TAAATCTATA TTATATTAGA CACTCTCTAA ACTATATATT TAACTACACC        2280

AATACTTTCT CCATCTAACC TTCGTCCTTG GTATAATTTA TTGCAAAGAG ACCCTTCAAT        2340

GAAGCAAACC ACATGGCATG TTTCCAAGTC ATATAATCAA ACGGCCATAA TCAAATCTAA        2400

AATATTCACA ATGTAGCACA AATCGTTCAA TATGTCCCAT ATCCAACTTA TTAAGGTGCT        2460

GGCTTTTGTT GGAGGGTTTT GAAAGGAGAC AAGTTTTGTC CCCACAATTG TTTCTCATGT        2520

GACCGACAAT TTCCTCTTAC TTGACCTGTC TTTGCTCCCA CTAAGTCCTT TTCTATTCAC        2580

TTATAATCTT TATGTATATA TAACATAACT AAACCCTTAT TTTCTTACAT GTTCAAAAAA        2640
```

```
TATTCCAACC CTAAAGAGAG TTAAAT ATG GCA AGA GAA GGT TTA GGA CTT GAG        2693
                            Met Ala Arg Glu Gly Leu Gly Leu Glu
                             1                5
```

```
ATA ACT GAG CTA AGG TTA GGT TTA TCA TGT GGT GAG CCA AAG AAG AAT        2741
Ile Thr Glu Leu Arg Leu Gly Leu Ser Cys Gly Glu Pro Lys Lys Asn
 10          15              20              25
```

```
GAG AAG AAG AGG ATG TTC TCG GAG ATC GAC GGT GGT GTG GAA GAA AAT        2789
Glu Lys Lys Arg Met Phe Ser Glu Ile Asp Gly Gly Val Glu Glu Asn
            30              35              40
```

```
GGA GGC TCC GGT GAT CGG AAA AGT GTC GAT AAG AAG AAT CAA GTT GTC        2837
Gly Gly Ser Gly Asp Arg Lys Ser Val Asp Lys Lys Asn Gln Val Val
                45              50              55
```

```
GGG TGG CCT CCG GTG TGC TCG TAC CGG AAG AAG AAC ATG AAT GAA GGT        2885
Gly Trp Pro Pro Val Cys Ser Tyr Arg Lys Lys Asn Met Asn Glu Gly
            60              65              70
```

```
TCG AAA ATG TAT ATG AAG GTT AGC ATG GAT GGA GCT CCT TAC TTG CGT        2933
Ser Lys Met Tyr Met Lys Val Ser Met Asp Gly Ala Pro Tyr Leu Arg
 75              80              85
```

```
AAG ATT GAT CTT TGT TTG CAT AAG GGT TAC TTG GAG TTA GCT TTG GCT        2981
Lys Ile Asp Leu Cys Leu His Lys Gly Tyr Leu Glu Leu Ala Leu Ala
 90              95              100             105
```

```
TTG GAG AAG CTC TTT GAT TGT TGT GGA ATT G GTGAGTTATG CATTTTTCAT        3032
Leu Glu Lys Leu Phe Asp Cys Cys Gly Ile
                110             115
```

```
TTTTTTTTTT TTTGTGTTTC ATCTTTTAAG TCTTTCTTAT TATTTGTGAT ACATGCAAAA        3092

TATAGGGCAT AATTCATTTT TAAAATATAA TGTATTGATT AGAGCATCTA TATTTATAAA        3152

GTAGTTGTCA AAATAATTAG TTAAATTGAA ATACAGATAT GATTGTACCC AAAAAAAATA        3212

CAGAATTATA GTATGATGAG TTTAATATGA ATTCTATTAA ATAAAAAATC TTACTATTTT        3272

TAGTAAATTT ATGATAAAAC ATCATATTTG TTCTTTTTTG TATTACTACA AAATTACTAA        3332

AAATGGTAAC GATTTTTCAT CCTTAAATTA TTTTTTAAAA GTCCATATTA AATTGATCCA        3392

GTAAAATATA CTATTGAAAA AATATTACTA ATATATAGAT CATTGATATC CTAAACTAAC        3452

AAATTTAATA AATATTTTTA ATATGATGTA TTTCTTATGA GAAATTTTTG TCACTCTAAA        3512

TATAAATTGT TTATTGTAAG TATTTCATCC GTTTTTTTAT TCAGTCAATT TAGAAAAAAT        3572

TGCACCAAAA TATATGTTGA TTTATAATAT TAATGAGTTA TTAATGATAT TTTTTTTTAT        3632

ATCTTAAATT ATTTTCAATT CTTAAATTTA ACTTTTCAAG ATTATTAATG AAGGAAATTT        3692

TATAAAATTA TAAAAAAAAT ATTTAAAATT AATTACTCCT CTTAATATAT AGTGTAGAAA        3752

AATTAAAACG ACTAATAATA AAAAAACAAA TTGAAGGAAG TATATCACAC AAATATAAGT        3812

GACTATGTGA GTAAGTTTTT TTATTATTAT TAATTGACAT TATAAAACTT CTTTACATGG        3872

CTATGGTTAG ATTATTATTA TATGAACTAA ATTATTTCTT ATATAAACTC AACACTCAAC        3932
```

```
AAACACTCAA GAAACCGGGA TATGATCGTT TATGTTTTTT ATGAAATAAA TATATGATTC    3992

TTTTATGTAA GTTAGGGTAT TGATCCCAGG TAGATATTAT TGTACAACAT ATAGGATCAT    4052

GAAGAATCTT TCATTTTTAT AAAGTTGATA GAAAAAAGGG TAAAGTGGGA GACAAAGTAT    4112

AATGTATAAT GATAATTAGA CATTCTCCTT CTAATCTGAT GCTCGCGTGC TGCTATTGTA    4172

CGTATAAAGT TCATCACTAC ATCTTAATGA CAAATAATCA AGCACAACAT TTATGCTACA    4232

TTAACATTAA TTAATCATAA CACTTGAATG AAAAGAAGGA AAAATAATAA TAATAAGAGT    4292

ATTGAAAATT AATTAAAATT TTATTTGTTG GCAG  AA GAG GCA TTA AAG GAT        4343
                                      Glu Glu Ala Leu Lys Asp
                                                            120

GCA GAA AAT TGT GAA CAC GTT CCA ATT TAT GAG GAC AAA GAT GGT GAT      4391
Ala Glu Asn Cys Glu His Val Pro Ile Tyr Glu Asp Lys Asp Gly Asp
            125                 130                 135

TGG ATG CTG GTT GGA GAT GTC CCT TGG GA GTAAGTACTT TTATCTATTT         4440
Trp Met Leu Val Gly Asp Val Pro Trp Glu
        140                 145

CCTATACTAT TATTTAATTT AATATAATTC TTTCTATTAT ACTATACAAA ATAAATCAAA    4500

TAAAAATTAT ATATATATAT ATATCTTGGA CCCCATATAG GAGACATGCG TGAACCTTTC    4560

ATTATAATAT GTTGAGAACA TTAATTTAGA AGGAGAAACA ATCAAAATGA TGGCCTACCA    4620

TGGAAAAGGA AAAGCCATTA TTGTGTTATG GAAACATCAA ATAAAGAGAG AGATTGCAAT    4680

TCCTATAATG ATCAAACATG AAAATTTTCT AAAATTAATA TGTAAAAGTA TATAGTATAG    4740

TAATTAATAT TCACTTTTAT GATGTGAAAA AAAACAG G ATG TTT ATT GAG TCA       4793
                                        Met Phe Ile Glu Ser
                                                        150

TGC AAG AGG CTG AGG ATT ATG AAG AGG TCA GAT GCA AAG GGC TTT GAT      4841
Cys Lys Arg Leu Arg Ile Met Lys Arg Ser Asp Ala Lys Gly Phe Asp
        155                 160                 165

TTG CAA CCA AAA GGA TCT TTG AAG AGA TTC ATA TAGAAAGTGA AAGATATGTT    4894
Leu Gln Pro Lys Gly Ser Leu Lys Arg Phe Ile
        170                 175

AGGGTTCTAA ACAATGAAAA AGTTGTTAAT TTGGATTTTA TGTTGTTTTT TAATTATATT    4954

TGAGAAGCAT TCCTTTATAC TATAGTTTGA TATGAATGAA CTAGGGTTTT ATCATCATGT    5014

TTATTTTAAT GTTTTATATA TCAAAGATAT ATAGGATCAA TTTTTATTAT GGATTTAAAG    5074

GATATGTATT GTGAGTGTTA TTTTGAATTT CTTCGGTTGA AGGGAAGAAA TACCTTTTTG    5134

TTACAAATTA TTTGTATAAT TTGATATAGC TTAGCCATTG TTAACTAGTA ATTAGGATCT    5194

TCATCCCTTC AATTTTTGGG CTTGCTAAAA ATCAGACCTT AAACACCATG TTGTTTAAAA    5254

AGTTATGTAA CTATATATTG CCGTTTTAGA AAATATAGAG GTTATATTCT AATTTTTAAA    5314

ATTGGCCATA ATAATAAAGA ATATTTTATT AAAATTATAA GTAATATTAA AAAATAAAGG    5374

AAAATAAATA AATTATTTAT AGATATGTTA ATAATATATT TGTCGTAGAT TTTTAATTAT    5434

TTATTTAAAT TTCAAAATTT TAAAGGTTTA ATATGTGATG GTTTATAGAT TCAATTAAT     5494

AATAGAAATT TTTGTATTTT TTATTAAGTT TATCGTTGAC TCACTGGTAT ATATCCTTCA    5554

TCAAGCCCTT CGGTACGCGA GTTCGATTTT ATATATTCGT TACGCTGTTT AAAGTTAACT    5614

AATTTATAAA TGCAACGAAT ATTATAAATA TAATTATTTA ATATTTATAC TTTATAAAAA    5674

AAATAAGGGT TGCTTTTTC GGAGGTCCTA TGTAACAGTT TGATTTTCG GAGGTCCTAT      5734

GTAACGGATC AGGTTACACA TGCTCAAATC CGGTCCCATA AATATATATA TAGGGTATGT    5794

TGTTTTAACT TTAAGAATAG ATTTTTGGAA AAAATATATT ATGGGTTCTT TAAGTTATTT    5854
```

```
AATTATAACA GTTTGGTCCT TTAATTTTTT TTACCGTGAG TCATTCCTTT AAGTTACCTA      5914

ACGTCTAGA                                                              5923
```

(2) INFORMATION FOR SEQ ID NO: 4:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..540
        (D) OTHER INFORMATION: /product= "PSIAA6 auxin-induced
            protein"
            /note= "Aux/IAA from pea
            (Pisum sativum)"

(xi) SEQUENCE DESCRIPTION: SEQ ID NO: 4:

```
ATG GCA AGA GAA GGT TTA GGA CTT GAG ATA ACT GAG CTA AGG TTA GGT        48
Met Ala Arg Glu Gly Leu Gly Leu Glu Ile Thr Glu Leu Arg Leu Gly
 1               5                  10                  15

TTA TCA TGT GGT GAG CCA AAG AAG AAT GAG AAG AAG AGG ATG TTC TCG        96
Leu Ser Cys Gly Glu Pro Lys Lys Asn Glu Lys Lys Arg Met Phe Ser
             20                  25                  30

GAG ATC GAC GGT GGT GTG GAA GAA AAT GGA GGC TCC GGT GAT CGG AAA       144
Glu Ile Asp Gly Gly Val Glu Glu Asn Gly Gly Ser Gly Asp Arg Lys
         35                  40                  45

AGT GTC GAT AAG AAG AAT CAA GTT GTC GGG TGG CCT CCG GTG TGC TCG       192
Ser Val Asp Lys Lys Asn Gln Val Val Gly Trp Pro Pro Val Cys Ser
     50                  55                  60

TAC CGG AAG AAG AAC ATG AAT GAA GGT TCG AAA ATG TAT ATG AAG GTT       240
Tyr Arg Lys Lys Asn Met Asn Glu Gly Ser Lys Met Tyr Met Lys Val
 65                  70                  75                  80

AGC ATG GAT GGA GCT CCT TAC TTG CGT AAG ATT GAT CTT TGT TTG CAT       288
Ser Met Asp Gly Ala Pro Tyr Leu Arg Lys Ile Asp Leu Cys Leu His
                 85                  90                  95

AAG GGT TAC TTG GAG TTA GCT TTG GCT TTG GAG AAG CTC TTT GAT TGT       336
Lys Gly Tyr Leu Glu Leu Ala Leu Ala Leu Glu Lys Leu Phe Asp Cys
            100                 105                 110

TGT GGA ATT GAA GAG GCA TTA AAG GAT GCA GAA AAT TGT GAA CAC GTT       384
Cys Gly Ile Glu Glu Ala Leu Lys Asp Ala Glu Asn Cys Glu His Val
        115                 120                 125

CCA ATT TAT GAG GAC AAA GAT GGT GAT TGG ATG CTG GTT GGA GAT GTC       432
Pro Ile Tyr Glu Asp Lys Asp Gly Asp Trp Met Leu Val Gly Asp Val
    130                 135                 140

CCT TGG GAG ATG TTT ATT GAG TCA TGC AAG AGG CTG AGG ATT ATG AAG       480
Pro Trp Glu Met Phe Ile Glu Ser Cys Lys Arg Leu Arg Ile Met Lys
145                 150                 155                 160

AGG TCA GAT GCA AAG GGC TTT GAT TTG CAA CCA AAA GGA TCT TTG AAG       528
Arg Ser Asp Ala Lys Gly Phe Asp Leu Gln Pro Lys Gly Ser Leu Lys
                165                 170                 175

AGA TTC ATA TAG                                                       540
Arg Phe Ile
```

(2) INFORMATION FOR SEQ ID NO: 5:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO: 5:

Met Ala Arg Glu Gly Leu Gly Leu Glu Ile Thr Glu Leu Arg Leu Gly
 1               5                  10                  15

Leu Ser Cys Gly Glu Pro Lys Lys Asn Glu Lys Lys Arg Met Phe Ser
                20                  25                  30

Glu Ile Asp Gly Gly Val Glu Glu Asn Gly Gly Ser Gly Asp Arg Lys
            35                  40                  45

Ser Val Asp Lys Lys Asn Gln Val Val Gly Trp Pro Pro Val Cys Ser
    50                  55                  60

Tyr Arg Lys Lys Asn Met Asn Glu Gly Ser Lys Met Tyr Met Lys Val
65                  70                  75                  80

Ser Met Asp Gly Ala Pro Tyr Leu Arg Lys Ile Asp Leu Cys Leu His
                85                  90                  95

Lys Gly Tyr Leu Glu Leu Ala Leu Ala Leu Glu Lys Leu Phe Asp Cys
                100                 105                 110

Cys Gly Ile Glu Glu Ala Leu Lys Asp Ala Glu Asn Cys Glu His Val
                115                 120                 125

Pro Ile Tyr Glu Asp Lys Asp Gly Asp Trp Met Leu Val Gly Asp Val
    130                 135                 140

Pro Trp Glu Met Phe Ile Glu Ser Cys Lys Arg Leu Arg Ile Met Lys
145                 150                 155                 160

Arg Ser Asp Ala Lys Gly Phe Asp Leu Gln Pro Lys Gly Ser Leu Lys
                165                 170                 175

Arg Phe Ile (2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "degradation signal motif
            targeting proteins for import into
            mammalian lysosomes in response to
            serum deprivation"

(xi) SEQUENCE DESCRIPTION: SEQ ID NO: 6:

Lys Phe Glu Arg Gln
 1               5

(2) INFORMATION FOR SEQ ID NO: 7:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "nuclear localization signal

```
            (NLS) from squash leaf curl virus BR1
            movement protein"

(xi) SEQUENCE DESCRIPTION: SEQ ID NO: 7:

Ser Tyr Val Lys Thr Val Pro Asn Arg Thr Arg Thr Tyr Ile Lys Leu
1               5                   10                  15

(2) INFORMATION FOR SEQ ID NO: 8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..57
        (D) OTHER INFORMATION: /note= "oligo #1"

(xi) SEQUENCE DESCRIPTION: SEQ ID NO: 8:

CTAGATCTTA CGTTAAGACT GTTCCAAACA GAACTAGAAC TTACATCAAG TTCTGAG         57

(2) INFORMATION FOR SEQ ID NO: 9:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..57
        (D) OTHER INFORMATION: /note= "oligo #2"

(xi) SEQUENCE DESCRIPTION: SEQ ID NO: 9:

GATCCTCAGA ACTTGATGTA AGTTCTAGTT CTGTTTGGAA CAGTCTTAAC GTAAGAT         57
```